(12) United States Patent
Kagan et al.

(10) Patent No.: US 9,072,887 B2
(45) Date of Patent: Jul. 7, 2015

(54) SELF-ADAPTIVE BIO-SIGNAL AND MODULATION DEVICE

(75) Inventors: Cherie Kagan, Bala Cynwyd, PA (US); Brian Litt, Bala Cynwyd, PA (US); Jonathan Viventi, New York, NY (US)

(73) Assignee: The Trustees Of The University of Pennsylvania, Philadelphia, PA (US)

( * ) Notice: Subject to any disclaimer, the term of this patent is extended or adjusted under 35 U.S.C. 154(b) by 805 days.

(21) Appl. No.: 13/321,339

(22) PCT Filed: May 20, 2010

(86) PCT No.: PCT/US2010/035584
§ 371 (c)(1),
(2), (4) Date: Feb. 14, 2012

(87) PCT Pub. No.: WO2010/135539
PCT Pub. Date: Nov. 25, 2010

(65) Prior Publication Data
US 2012/0143568 A1  Jun. 7, 2012

Related U.S. Application Data

(60) Provisional application No. 61/179,843, filed on May 20, 2009.

(51) Int. Cl.
*H03F 1/26* (2006.01)
*A61N 1/05* (2006.01)
*A61N 1/36* (2006.01)

(52) U.S. Cl.
CPC .......... *A61N 1/0529* (2013.01); *A61N 1/36082* (2013.01)

(58) Field of Classification Search
CPC .......... A61N 1/0529; A61N 1/36082
See application file for complete search history.

(56) References Cited

U.S. PATENT DOCUMENTS

| | | |
|---|---|---|
| 6,284,562 B1 | 9/2001 | Batlogg |
| 6,335,539 B1 | 1/2002 | Dimitrakopoulos |
| 6,569,707 B2 | 5/2003 | Dimitrakopoulos |
| 6,963,080 B2 | 11/2005 | Afzali-Ardakani |

(Continued)

FOREIGN PATENT DOCUMENTS

WO   WO-2009114689 A1   9/2009

OTHER PUBLICATIONS

International Application Serial No. PCT/US10/35584, International Search Report mailed Jul. 29, 2010, 1 pg.

(Continued)

*Primary Examiner* — Elias Desta
(74) *Attorney, Agent, or Firm* — RatnerPrestia

(57) ABSTRACT

A sensor-effector system includes an array of sensor-effector transducers providing a plurality of sensed signals and applying a plurality of effector signals. The array provides signals to input signal conditioning circuitry which digitizes and filters the plurality of sensed signals. A processor receives the digitized signals, and processes them to generate multiple feature vectors. It also analyzes the feature vectors to identify patterns and classify the identified patterns and generates at least one response vector resulting from the recognized pattern. The response vector is applied to output signal conditioning circuitry, coupled which converts the response vector to at least one analog signal which is applied as an effector signal to the array of sensor-effector transducers.

20 Claims, 4 Drawing Sheets

(56) References Cited

U.S. PATENT DOCUMENTS

| | | | |
|---|---|---|---|
| 7,125,989 | B2 | 10/2006 | Afzali-Ardakani |
| 8,097,926 | B2 * | 1/2012 | De Graff et al. ............. 257/419 |
| 2003/0186461 | A1 | 10/2003 | Boehr |
| 2004/0183070 | A1 | 9/2004 | Afzali-Ardakani |
| 2007/0173897 | A1 | 7/2007 | Zdeblick |
| 2008/0012007 | A1 | 1/2008 | Li |
| 2008/0081769 | A1 | 4/2008 | Hassibi |
| 2009/0001355 | A1 | 1/2009 | Afzali-Ardakani |

OTHER PUBLICATIONS

Agner, Shannon C., "Segmentation and Classification of Triple Negative Breast Cancers Using DCE-MRI", IEEE International Symposium on Biomedical Imaging (ISBI), (2009), 1227-1230.

Anthopoulos, Thomas D., "Electro-Optical Circuits Based on Light-Sensing Ambipolar Organic Field-Effect Transistors", Applied Physics Letters, vol. 91 (2007), 113513-1-113513-3.

Bartic, Carmen, "Organic Thin-Film Transistors as Transducers for (Bio)Analytical Applications", Anal Bioanal Chem, vol. 384 (2006), 354-365.

Burges, Christopher J.C., "A Tutorial on Support Vector Machines for Pattern Recognition", Data Mining and Knowledge Discovery, vol. 2 (1998), 121-167.

Chan, Heang-Ping, "Computerized Classification of Malignant and Benign Microcalcifications on Mammograms: Texture Analysis Using an Artificial Neural Network", Phys. Med, Biol., vol. 42 (1997), 549-567.

Cortes, Corinna, "Support-Vector Networks", Machine Learning, vol. 20 (1995), 273-297.

Diorio, Chris, "A Floating-Gate MOS Learning Array with Locally Computed Weight Updates", IEEE Transactions on Electron Devices, vol. 44, No. 12 (Dec. 1997), 10 pgs.

Feili, D., "Organic Field Effect Transistors for Neural Stimulation—In Vitro Tests", 10th Annual Conference of the International FES Society (Jul. 2005), 3 pgs.

Feili, D., "Flexible Mircoelectrode Arrays with Integrated Organic Semiconductors", 9th Annual Conference of the International FES Society (Sep. 2004), 3 pgs.

Feili, Dara, "Flexible Organic Field Effect Transistors for Biomedical Microimplants Using Polyimide and Parylene C as Substrate and Insulator Layers", J. Micromech. Microeng., vol. 16 (2006), 1555-1561.

Feili, Dara, "Encapsulation of Organic Field Effect Transistors for Flexible Biomedical Microimplants", Sensors and Actuators A, vol. 120 (2005), 101-109.

Forrest, Stephen, "The Path to Ubiquitous and Low-Cost Organic Electronic Appliances on Plastic", Nature, vol. 428 , (Apr. 29, 2004), 911-918.

Jackson, Alan, "Imaging Tumor Vascular Heterogeneity and Angiogenesis using Dynamic Contrast-Enhanced Magnetic Resonance Imaging", Clin. Cancer Res., vol. 13, No. 12, (Jun. 15, 2007), 3449-3459.

Rost, Constance, "Ambipolar Light-Emitting Organic Field-Effect Transistor", Applied Physics Letters, vol. 85, No. 9, (Aug. 30, 2004), 1613-1615.

Saul, Lawrence K., "An Introduction to Locally Linear Embedding", Retrieved from the Internet: <URL: http://es.nyu.edu/~roweis/11e/papers/lleintro.pdf > (2000) 13 pgs.

Schwarz, M., "Organic Semiconductors Providing New Solutions for Future Medical Implants", IEEE 2005, Polytronic 2005, 5th International Conference on Polymers and Adhesives in Microelectronics and Photonics, 78-81.

Yan, Shuicheng, "Graph Embedding: A General Framework for Dimensionality Reduction", IEEE Computer Society Conference on Computer Vision and Pattern Recognition, 2005 (Jun. 20-25, 2005) 830-837.

* cited by examiner

SELF-ADAPTIVE BIO-SIGNAL AND MODULATION DEVICE

This application is a U.S. National Phase application of PCT Application No. US2010/035584, filed May 20, 2010, and published in English Nov. 25, 2010, as WO 2010/135539, which claims priority to U.S. Provisional Application No. 61/179,843, filed May 20, 2009, each of which is incorporated herein by reference in its entirety for all purposes.

BACKGROUND OF THE INVENTION

The subject invention is embodied in a system for identifying and treating patterns of signals in a biologic structure.

There is a need to develop implantable devices to treat a host of neurological and psychiatric conditions such as stroke, epilepsy, movement disorders, depression, and schizophrenia that afflict hundreds of millions of people worldwide. Central to this task is understanding the functional biological networks disrupted by these disorders, and their response to injury and disease. Current implantable brain devices, for example, typically are not designed with these concepts in mind. They may crudely stimulate large regions of brain, without sensing, and may not be able to access the fine multi-scale architecture comprising brain function: from single cells and cortical columns, to deep brain nuclei and dispersed, interconnected cortical regions. They may also be incapable of interacting with the brain's native neuroplasticity, its capacity for self-reorganization and repair. Therefore, as a prerequisite to making intelligent implantable devices to treat disease, it may be desirable to develop an understanding of the basic behavior of large, distributed biological neural networks in response to specific types of challenges. A barrier to obtaining comprehensive data to that end is technological.

SUMMARY OF THE INVENTION

The present invention is embodied in an array of sensor-effector transducers for providing a plurality of sensed signals and for applying a plurality of effector signals. The sensor-effector array provides signals to input signal conditioning circuitry which digitizes the plurality of sensed signals. A processor receives the digitized signals, and processes them to generate multiple feature vectors. It also analyzes the feature vectors to identify patterns and classify the identified patterns. In addition, the processor generates at least one response vector resulting from the recognized pattern. The response vector is applied to output signal conditioning circuitry, which converts the response vector to at least one analog or digital signal which is applied as an effector signal to the array of sensor-effector transducers.

According to one aspect of the invention, the array of sensor-effector transducers is implemented using organic semiconductor devices.

According to another aspect of the invention, the processor is configured to analyze signals obtained from the sensors in the array of sensor-effector transducers to classify patterns of signals and to control the effectors in the array of sensor-effector transducers, based on the classified patterns to modify the operation of the sensor-effector array.

DETAILED DESCRIPTION OF THE INVENTION

Figure 1:
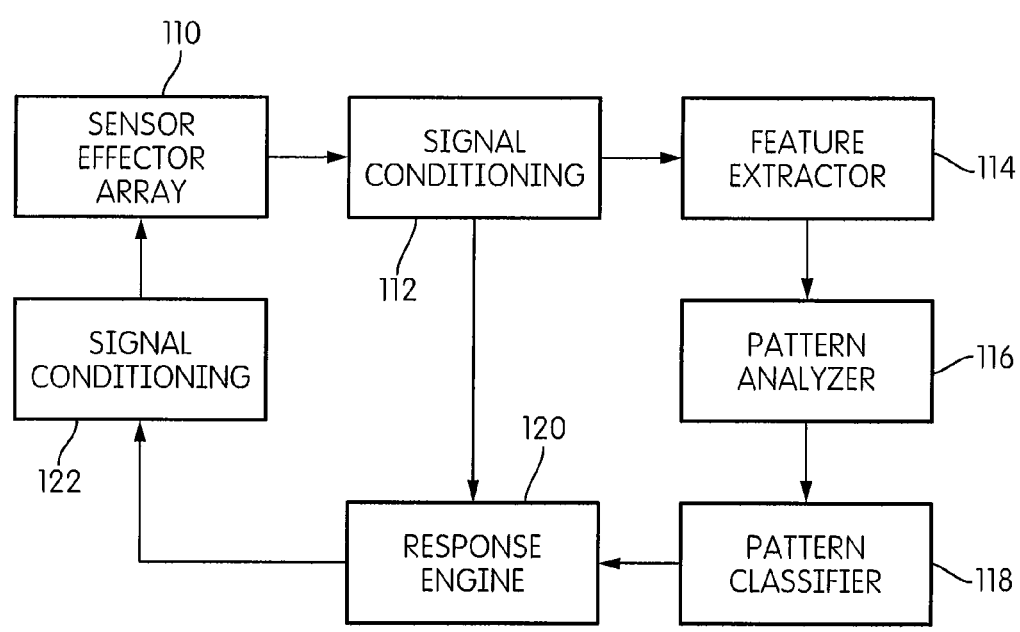
FIG. 1 is a block diagram of an example sensor-effector system.

One example embodiment of the invention is a scalable, self-adaptive brain computer interface (BCI) platform to explore the architecture and operation of multi-scale, functional brain networks. Devices built upon this platform enable the mapping of dynamic networks in normal and disease states, and the emulation of network plasticity. As they sample multi-scale electrical and optical signals at high-resolution, these devices dynamically alter their sensor and effector configurations, and use machine learning algorithms to produce specific outputs for neuromodulation which in the future may be directed for therapeutic purposes.

High-density microelectrodes, optical, chemical and other types of transducers that may be implemented using a flexible electronic platform are configured in architectures that self-modify their temporal and spatial recording characteristics and stimulation outputs according to the neural inputs they transduce. Active electronics may be placed over large brain areas coupled to thousands of multi-scale (i.e. from nanometer to centimeter scale), individually addressable recording electrodes, photosensors and chemical sensors. These transducers are fabricated on flexible, stretchable substrates that conform to, and interact with the brain. This arrangement mitigates the limited spatial and temporal sampling of current generation brain-computer interface devices that rely on passive technology. Using machine learning and data mining algorithms, the devices "learn" the brain's response patterns to controlled sensory stimuli or to injury and disease progression, as well as those associated with regaining function. The devices adapt to ongoing activity patterns and generate outputs that compensate for changes in neural signals accompanying deterioration or loss of function, mimicking native neuroplasticity.

In addition to its therapeutic functions, this embodiment may have direct and broad implications for research and the testing of experimental models. For example, this embodiment may be used to study the process of epileptogenesis, in which prolonged or repeated occurrence of seizures and their precursors modify neural circuits through neuroplasticity, making the brain epileptic. Similarly, this embodiment may be used to test sets of circuit alterations that characterize a variety of other neurological diseases, including depression, movement disorders, epilepsy, obesity, addiction, schizophrenia and its neurological models (such as in ketamine-induced dissociated states in rodents, and in Neuroregulin knockout mice). Patterned electrical stimulation adapted to the activity of the particular disease network under study, governed by machine learning algorithms, may be used to arrest epileptogenesis and prevent seizures or, to reverse symptoms and oscillations associated with schizophrenia and other diseases as well as in animal models of and animals affected with these disorders. Understanding how specific spatial and temporal signatures of brain activity are altered in each of these conditions, and correcting them is a key step towards manipulating these cellular and multi-scale brain activity to drive the system toward states of more normal function.

One feature of the example embodiment is its ability to conform to the physical shape of brain tissue, specifically to conform to the gyral and sulcal patterns in the brain. It may also be configured to completely coat and cover a variety of contact and penetrating sensor/effector elements and other device structures. In addition, the array may be configured to make contact with and control implanted devices that are not a part of the array but that are configured to interface with the array to receive and provide data signals and/or control signals. To achieve this function, the example embodiment sensor-effector array is formed using organic semiconductors formed as a thin, flexible array of transducers, which can function as sensors or stimulators, photo-sensors and photo-emitters. It is contemplated, however, that not all of these types of transducers are needed and that other types of transducers, for example pressure transducers may be used in the array.

Organic semiconductors continue to receive attention as the active channels in thin-film transistors (TFTs) for low-cost, large-area, printable and flexible electronics. A variety of organic circuits, such as displays, RFID tags, sheet-type imagers, memories, and pressure sensor arrays, have been fabricated on flexible substrates. The example embodiments of the subject invention combine organic transistors, sensing circuits, and implantable devices to produce flexible circuits that conform to the brain and enable high-density recording of physiological signals and effecting of neuronal circuits to map normal brain function and treat brain network disorders.

FIG. 1 is a block diagram of a system including an example embodiment of the invention. In FIG. 1, a sensor-effector array 110, formed on a flexible substrate that is configured to conform to brain tissue, receives electrical, optical and chemical signals from the brain and provides electrical, optical and chemical stimulus to the brain. The electrical, optical and chemical signals provided by the sensor-effector array 110 are converted to electrical signals which are applied to signal conditioning circuitry 112. The circuitry 112 may, for example, include preamplifiers (not shown), analog-to-digital converters (ADC's) (not shown), spatial filters (not shown) and temporal filters (not shown). Output signals provided by the signal conditioning circuitry 112 may include, for example, digital signals representing instantaneous voltage values measured at individual electrodes, indications of specific chemical compounds sensed by individual chemical sensors and light values sensed by individual optical sensors in multiple frequency bands and spatial maps of sub-arrays of the sensors in the sensor-effector array 110. The signal conditioning circuitry may also include filters to reduce the effects of interfering ambient noise signals and signals generated by the brain tissue that are not of interest to a particular diagnosis and/or therapeutic use of the device. The sensor-effector array 110 may also include digital circuitry and may provide digital signals directly to the feature extractor 114, pattern analyzer 116, pattern classifier 118 and/or response engine 120.

The system shown in FIG. 1 may be partly or entirely implemented within the body of a patient. For example, the sensor-effector array 110 may be coupled to the patient's brain and may be connected to the remaining circuitry shown in FIG. 1 via, for example, inductive coupling or radio frequency telemetry. Alternatively, all of the circuitry shown in FIG. 1 may be implemented within the cranial cavity of the patient further including a battery (not shown) and an inductively coupled battery charger which allows the battery to be recharged through the skin.

The output signals provided by the signal conditioning circuitry 112 are applied to a feature extractor 114 which processes the signals into features that may be useful for the pattern analyzer 116 and pattern classifier 118, described below. Exemplary features may include, for example, spatial and temporal correlations among individual signals, signals having time-domain, frequency domain, wavelet domain and/or chaotic domain values that exceed predetermined threshold values and/or are in predetermined ranges. After feature extraction, the classifier may combine multiple features provided by the signal conditioning circuitry using a variety of machine learning methods including, but not limited to, support vector machines, k-means clustering, hidden Markov models, genetic and Bayesian methods and fuzzy clustering. The result to provide one or more signals for decision making regarding therapy, reorganization of recording parameters, choice of sensors and decisions on potential on-the-fly changes in feature selection. The pattern analyzer 116 and pattern classifier 118 may use hybrid features and features of features in addition to the features provided by the signal conditioning circuitry 112. For example, the feature extractor may generate histograms of signals or groups of signals in the time domain and/or frequency domain. It may also identify statistical features, such as the mean and standard deviation of a particular signal or group of signals. The feature extractor may also pass signals produced by the signal conditioning circuitry without modification to the pattern analyzer 116. The feature extractor 114 may be implemented using statistical and/or signal processing software running on a digital signal processor or general-purpose computer.

The exemplary feature extractor 114, pattern analyzer 116, pattern classifier 118 and response engine 120 form the center of "intelligence" of the device. This intelligence then controls algorithm-driven changes in device configuration, sensor and effector parameters (plasticity) of the example BCI-device platform. These modules include machine learning algorithms to extract, combine and classify features from multi-scale neuronal activity (e.g. neurotransmitter measurements, multi-unit, local fields, field potentials, EEG, etc.) and to look for fixed functional relationships across scales that might divulge basic relationships between integration of neuronal activity at different levels. The pattern analyzer 116 and pattern classifier 118 may implement one or more of several classification functions which the inventors have found useful for interpreting neuronal states these include: Hidden Markov Models, Support Vector Machines, and Frequent Itemset Mining. An example Hidden Markov Model system is described in a publication by S. Wong, A. B. Gardner, A. M. Krieger, B. Litt, "A Stochastic Framework for Evaluating Seizure Prediction Algorithms Using Hidden Markov Models," J. Neurophysiology 97(3): 2525-2532 (2007). An example Frequent Itemset Mining system is described in a publication by A. B. Gardner, A. M. Krieger, G. Vachtsevanos, B. Litt, entitled "One Class Novelty Detection for Seizure Analysis from Intracranial EEG," J. Machine Learning Research 7 1025-1044, (2006). An example Support Vector Machine algorithm is described in a publication by H. Firpi, O. Smart, G. Worrell, E. Marsh, D. Dlugos and B. Litt, entitled "High Frequency Oscillations Detected in Epileptic Networks Using Swarmed Neural-network Features," Ann. Biomed. Engin. 35(9): 1573-1584, (2007).

Outputs from one or more of these classifiers are conditioned in the response engine 120 and signal conditioning circuitry 122 to guide multi-focal feedback effector activation (including chemical release, stimulation and other forms of network/cellular activity modulation) according to specific learning rules to drive neurophysiological inputs back to the healthy state. The response engine 120 may receive signals from the sensor/effector array provided by the signal conditioning circuitry 112 in order to effectively monitor feedback. For each neurological condition being analyzed or treated, candidate features provided by the feature extractor 114, analyzed by the pattern analyzer 116 and classified by the pattern classifier 118 may be tested for statistical impact on pattern classification. Feature sets may be pared down to a group of individual parameters with significant statistical impact. New learning rules and systems may be applied to allow implementation of pattern classification and stimulus control through the response engine 120 and signal conditioning circuitry 122. It is contemplated that Small World and Scale-Free networks may be used to model multi-scale neural inputs in useful structures, as these models may offer new strategies for intervention not suggested by machine learning algorithms, such as identifying attack points for intervention.

Alternatively or in addition to the predetermined controls, the signals provided by the response engine 120 and signal conditioning circuitry 122 to the sensor/effector array 110 may be randomized about a predetermined set of actuation functions to prevent the feedback algorithm from converging on a local minimum.

Figure 2:
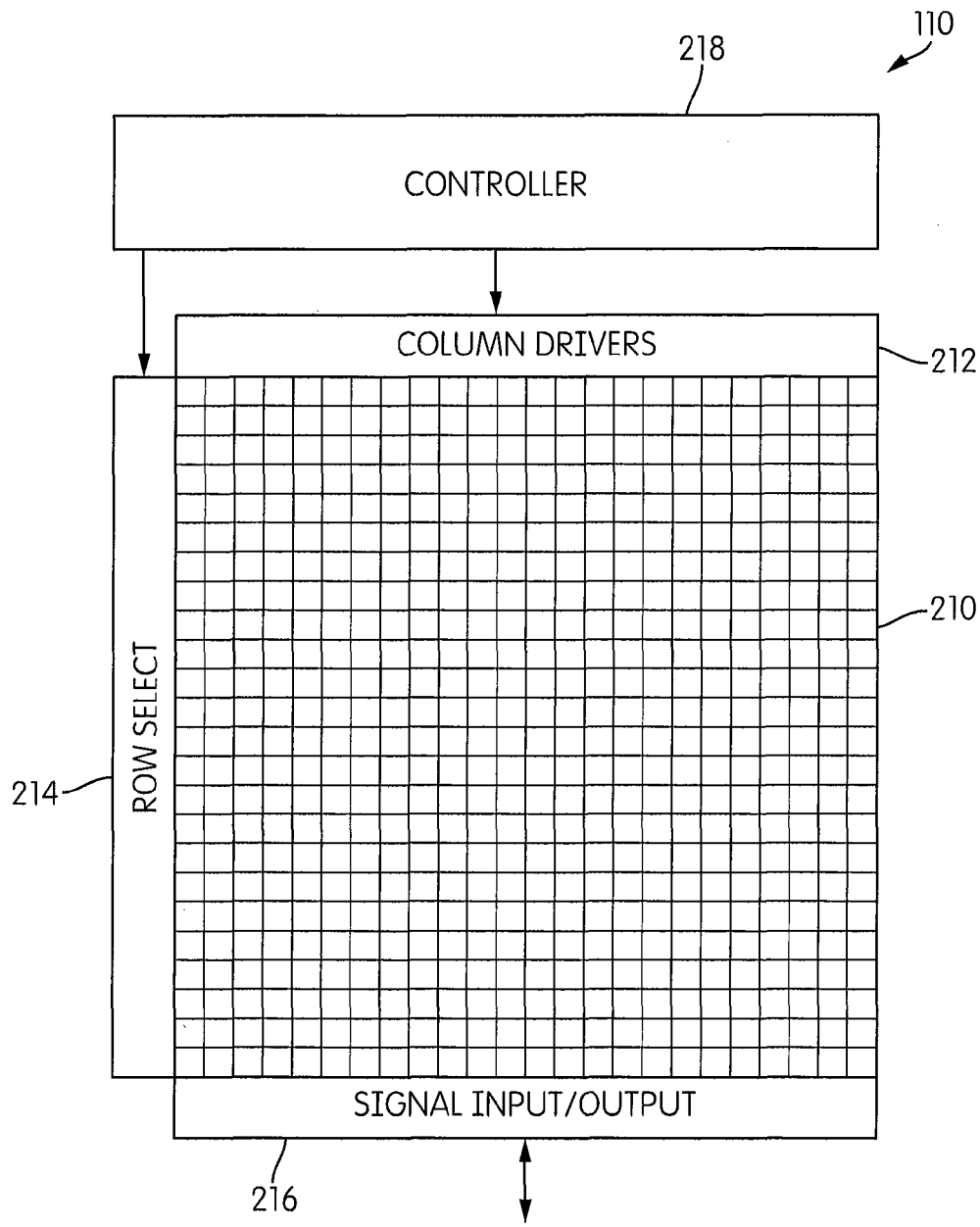
FIG. 2 is a block diagram of a sensor-effector array suitable for use in the system shown in FIG. 1.

FIG. 2 is a block diagram of a sensor/effector array 110 suitable for use with the example embodiment. The example array 110 includes an array of transducers 210, column driving circuitry 212, row select circuitry 214, signal input/output (I/O) circuitry 216 and a controller 218.

The example transducer array includes electrical sensor-effector transducers as well as chemical sensor-effectors, optical emitters and optical sensors. These are described below with reference to FIGS. 3A through 3D. The column driver circuitry includes conventional circuitry (not shown) that generates column select signals for individual columns, responsive to signals provided by the controller 218. The circuitry 212 also includes reset circuitry (not shown) which generates reset signals for the optical sensors. It is contemplated that the optical sensors of the sensor array 110 may be reset using a sliding window protocol to allow for maximum integration time for each of the optical sensors.

The row select circuitry may include a rolling shift register (not shown) that sequentially produces row select signals for each row of the array. Alternatively, the row select circuitry 214 may be controlled by the controller 218 to dynamically select one or more rows of the array. This may be useful to concurrently apply signals to a predetermined set of electrodes, chemical effectors or optical emitters in the array.

The signal I/O circuitry 216 may include preamplifiers and CCD shift registers to convert parallel sensed signals from the array of transducers 210 into a serial stream of analog values that are applied to the signal conditioning circuitry 112. Alternatively, the I/O circuitry 216 may include ADC circuitry that converts the analog values to digital values on the array 110 so that the array 110 provides a serial stream of digital values to the signal conditioning circuitry 112.

The I/O circuitry 216 may also include multiple oscillators (not shown) at different frequencies that may be used to impose a time-varying signal on tissue being monitored. The multiple oscillators may, for example, be coupled by respective busses to each column of the transducer array 210. Each of the columns, in turn, may include multiplexing circuitry (not shown) controlled by values provided by the controller 218 to select one of the oscillatory signals, responsive to signals provided by the response engine 120. Each multiplexer may be coupled to provide other signals, for example, fixed potential signals. The signals provided by the multiplexing circuitry may be applied to either the electrical transducers or the chemical or optical emitters, as described below. Each of the multiplexers may include a register, coupled in series to other registers and to the controller 218 so that the controller 218 may load control values to determine which signals are applied to the chemical emitters, optical emitters and electrical transducers. The response engine 120, shown in FIG. 1, may transmit digital signals CONT that are applied directly to the sensor-effector array 110 to define how the controller 218 controls the multiplexers and other circuitry in the array that determines its configuration. Similarly, the sensor effector array 110 may provide digital signals directly to the feature extractor 114, pattern analyzer 116, pattern classifier 118 and response engine 120. These signals may, for example, define the current state of the sensor-effector array 110, including the current connectivity provided by the multiplexers.

Figure 3A:
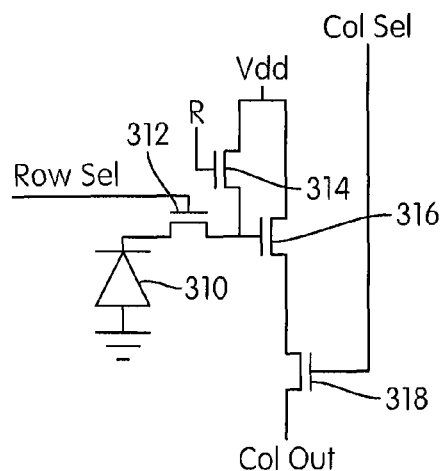
FIGS. 3A, 3B, 3C and 3D are schematic diagrams of various sensor-effector transducers that may be used in the sensor-effector array shown in FIG. 2.

FIG. 3A is a schematic diagram of an example photosensor suitable for use in the sensor-effector array 210, shown in FIG. 2. The photosensor includes a photodiode 310, a row-select transistor 312, a reset transistor 314, a source-follower amplifier transistor 316 and a column select transistor 318. In operation, when row-select transistor 312 is turned on, the reset signal, R, is asserted to reset the photodiode 310. This signal reverse-biases the photodiode, creating a depletion region. Subsequently, during an integration period, photons passing through the photodiode generate photo-electrons which increase the charge in the depletion region. At the end of the integration period, the row-select signal is again asserted to transfer the accumulated charge on the photodiode to the gate electrode of the source-follower transistor 316. The column select signal is then asserted to read-out an electrical signal proportional to the stored charge.

Figure 3B:
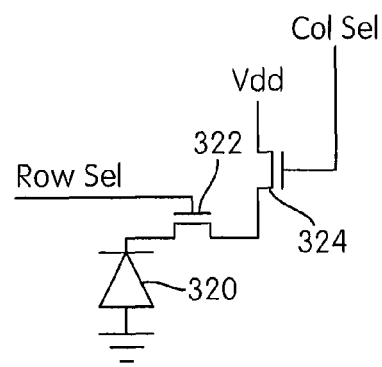

FIG. 3B is a schematic diagram of an example photo-emitter suitable for use in the array 210. In this circuit, an organic light-emitting diode (OLED) 320 is coupled to a row select transistor 322 and a column select transistor 324. When both the row-select transistor 322 and the column select transistor 324 are asserted, the OLED emits light. In the example sensor-effector array, the light emitters and sensors operate at the same time. It is contemplated that they may be configured in the sensor array such that each light sensor is adjacent to at least one light emitter. The light sensors may be used, for example, to detect blood oxygenation using pulse oximetry. The optical sensors may also be used to detect heart rate or to monitor changes in brain tissue that result in a change in color or light transmission.

As an alternative to using a separate photosensor and photo-emitter, it is contemplated that a single ambipolar transistor may be configured to perform both functions, although not at the same time. When the source electrode of the transistor is coupled to a reference potential (e.g. ground), the gate electrode is negatively biased and the drain electrode is even more negatively biased, the drain of the transistor injects minority carrier electrons into the channel. Because of the biasing arrangement, the channel acts as if it were a p-channel forming a pn junction. In this configuration, the excess carriers emit light. As a photo-sensor, the same transistor may be biased such that the device near the cusp in the off point (in ID-VG). In this configuration, the gate is sensitive to light. Other methods may also be used to configure ambipolar transistors as photo-sensors and photo-emitters. An example photo-emitter is described in an article by C. Rost et al. entitled "Ambipolar Light-Emitting Organic Field-Effect Transistor" *Applied Physics Letters* vol. 85, no. 9 August 2004. An example photo-sensor is described in an article by T. Anthopoulos entitled "Electro-optical circuits based on light-sensing ambipolar organic field-effect transistors," *Applied Physics Letters* vol. 91 no. 11 2007. While a single ambipolar transistor may be used both as a photosensor and photo emitter, separate ambipolar transistors may also be used. In this construction, each ambipolar transistor may be optimized for its chosen function as described in the above-referenced articles.

Figure 3C:
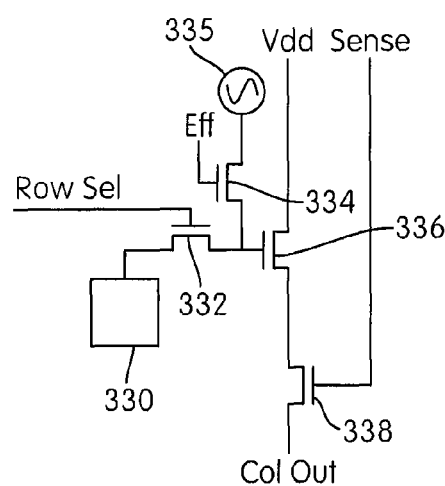

FIG. 3C is a schematic diagram of an example sensor-effector transducer suitable for use in the sensor-effector array 210. The example transducer includes a biocompatible surface electrode 330, a row-select transistor 332, an effector transistor 334, a signal source 335, a source-follower amplifier 336 and a column select transistor 338. When operated as a sensor, the row-select transistor 332 and column select transistor 338 are both turned on. Electrical signals or analytes sensed by the surface electrode 330 produce electrical signals that are passed to the gate of the source-follower transistor 336 which provides an amplified signal to the signal I/O circuitry 216, shown in FIG. 2.

When operated as an effector, the column select transistor is turned off and the row-select transistor is turned on. The effector transistor 334 is turned on, applying the signal supplied by the signal source 335 to the surface electrode 330. The signal source 335 may be implemented in the signal I/O circuitry 216 and may include multiple oscillators, voltage and/or current sources, coupled to a conductor that extends along a column of the sensor-effector array 210 by a multiplexer (not shown), as described above. The amplitude of the signal provided by the effector array may be controlled, at least in part, by controlling the magnitude of the effector signal, Eff. This signal may originate in the column driver circuitry 212, shown in FIG. 2, and may be coupled to the sensor-effector transducers by a column conductor that is independent of the output column bus, sense conductor, and signal conductor.

The sensor shown in FIG. 3C may also be used as a chemical sensor. As described in more detail below, the chemical sensing mechanism may be based on the change in conductivity in an organic semiconductor induced by direct interaction with certain molecules or by indirect reaction via the field effect in response to exposure to a particular analyte species. The sensor shown in FIG. 3C may be adapted to act as a chemical sensor by replacing the electrode 330 with an organic semiconductor which reacts with a chemical compound to be sensed. The electrode may also be connected to a reference voltage source (e.g. Vdd) as shown in phantom in FIG. 3C. It is contemplated that several different sensors of this type may be implemented, each using a respectively different organic semiconductor material as the electrode 330. The materials may be selected to produce reactions with various chemicals expected to be encountered. The measured impedance of all of the electrodes 330 may then provide a signature of a chemical that is sensed.

Figure 3D:
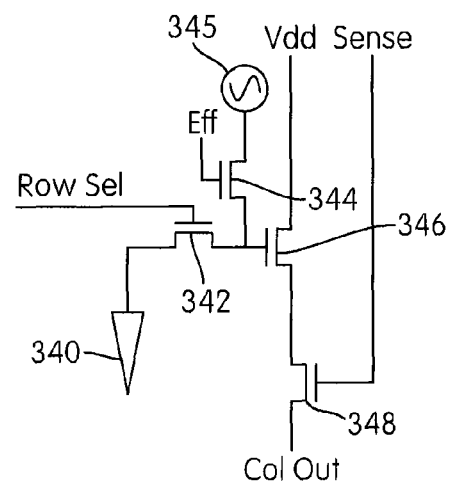

FIG. 3D is a schematic diagram of another example sensor-effector transducer. This transducer is identical to that shown in FIG. 3C except that the biocompatible electrode 340 is configured to extend into the brain tissue. The electrode may be configured to sense signals in a sulcus of the brain or it may pierce the brain tissue to sense a signal from one or more layers of the cortex or subcortical white matter or other structures or tissue. In addition to the electrode 340, the example circuit shown in FIG. 3D includes a row-select transistor 342, an effector transistor 344, a signal source 345, a source-follower transistor 346 and a column select transistor 348. Each of these elements operates in the same way as its corresponding element described above with reference to FIG. 3C.

Figure 4A:
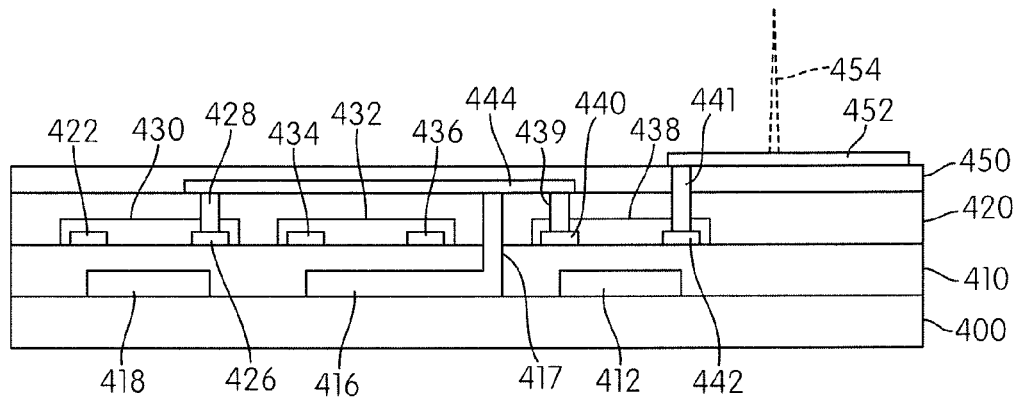
FIGS. 4A, 4B, 4C and 4D are cross-section diagrams of example thin-film organic semiconductor devices corresponding to the sensor-effector transducers shown in FIGS. 3A, 3B, 3C and 3D.

FIG. 4A (not to scale) shows in cross-section a diagram of an example embodiment of a sensor-effector circuit in accordance with the present invention. An array of sensor-effector transducers may be comprised of a plurality of such flexible electrical sensor-effector circuits and a flexible substrate 400. Each flexible electrical sensor-effector circuit may comprise:
  a first flexible transistor formed on the flexible substrate 400 having source electrode 422 and drain electrode 426 defining a first conductive path and a first gate electrode 418 configured to control the conductivity of the first conductive path;
  a second flexible transistor formed on the substrate 400 having source electrode 434 and drain electrode 436 defining a second conductive path and a second gate electrode 416 configured to control the conductivity of the second conductive path;
  a sensor-effector transducer 444 coupled to the drain electrode 426 of the first transistor and to the gate electrode 416 of the second transistor, wherein the first transistor is coupled to an effector circuit and the second transistor is coupled to a sensor circuit;
  a flexible select transistor having a conductive path defined by a source electrode 440 and a drain electrode 442 and a select gate electrode 412 configured to control the conductive path of the select transistor, wherein the source electrode 440 of the select transistor is coupled to the sensor-effector transducer 444 and the drain electrode 442 of the select transistor is coupled to the drain electrode 426 of the first transistor and to the gate electrode 416 of the second transistor and wherein the select gate electrode 412 is coupled to a select signal and configured to control the conductive path of the select transistor in response to the select signal.

Figure 4B:
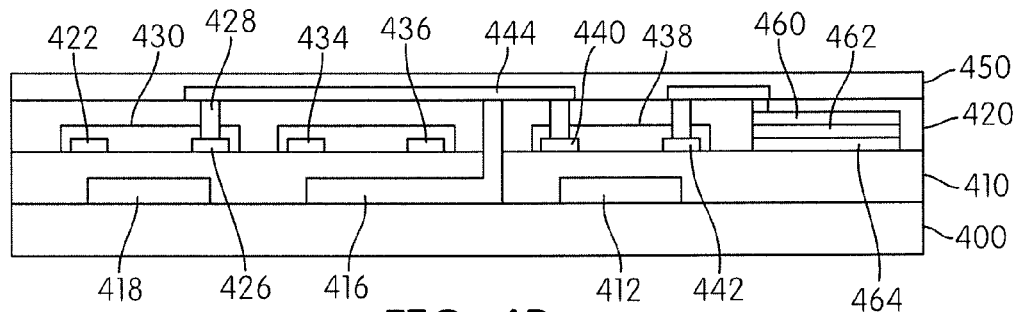
Figure 4C:
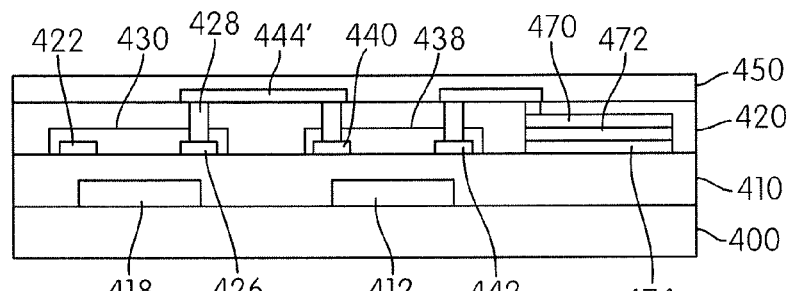

Gate electrodes 412, 416 and 418 are formed on flexible substrate 400. Gate electrodes 412, 416 and 418 may be comprised of any conventional gate conductor known in the art, including, for example, a conductive metal such as aluminum, tungsten, copper, gold, silver, palladium, platinum or chromium, indium tin oxide or polysilicon, conductive carbon (e.g., carbon nanotubes) or an organic conductor such as polyaniline or poly(3,4-ethylenedioxythiophene):polystyrene sulfonate (PEDOT:PSS). The gate electrodes may be formed by first depositing or growing the gate material and then patterning the same using conventional photo-lithography and etching techniques or by deposition through a shadow mask. Conventional deposition processes that can be used in forming the gate electrodes include, but are not limited to, chemical vapor deposition, plasma-assisted chemical vapor deposition, sputtering, evaporation, electroplating, electroless plating or other such deposition processes. When polysilicon is used, the doping may take place during the deposition process using an in-situ process or after, using ion implantation and annealing. Other, less conventional deposition methods may also be used such as, for example, ink-jet and gravure printing as well as other printing techniques employing inks or pastes containing metals, metal precursors or conductive polymers. FIGS. 4A-4C show transistors in which the source and drain contacts are on the bottom of the semiconductor layer, for example, contacts 422 and 426 are on the bottom of semiconductor layer 430. It is contemplated, however, that these contacts may be placed on top of the semiconductor layer, spaced away from the interface between the semiconductor layer 230 and the dielectric layer 410. It is also contemplated that the gate electrode may be placed on top of a dielectric layer formed above the semiconductor layer. This structure may be used either when the source and drain electrodes are beneath the semiconductor layer or on top of the semiconductor layer.

Substrate 400 is desirably fabricated using a material that is sufficiently flexible that the sensor-effector circuit assembly or array of such assemblies is capable of readily conforming to non-planar or irregularly shaped surfaces, such as those frequently encountered in implanting such an assembly or array into a human body, so that the assembly or array can come into intimate contact with an organ such as the brain. In some embodiments of the invention, substrate 400 is also stretchable (i.e., capable of being elongated without breaking or cracking). The material used for flexible substrate 400 should be sufficiently strong and tough that it is capable of withstanding manipulation and flexing without cracking or other mechanical deterioration and should also be biocompatible and biostable. The thickness of flexible substrate 400 may be varied as desired, consistent with the goal of maximizing flexibility, but typically is from about 2 to about 10 microns. Preferably, substrate 400 is fabricated from a polymer such as a plastic or rubber (elastomer). Polyimides are particularly useful in this regard, although other suitable illustrative flexible substrate materials include polyesters (e.g., polyethylene terephthalate), polycarbonates, polysilicones, polyacrylates and the like. In one embodiment of the invention, flexible substrate 400 is first formed as a thin film on a more rigid substrate (or is adhered to a more rigid substrate) such as an Si-containing substrate, glass substrate or plastic substrate and then later separated from the more rigid substrate (after a portion or all of the sensor-effector circuit has been assembled, for example). For example, a silicon wafer or glass substrate can be used as a mechanical carrier for assembling the desired sensor-effector circuit or array of such sensor-effector circuits.

Gate insulator 410 is comprised of any of the conventional dielectric materials known in the art, although preferably such a material is flexible and thus is advantageously selected from organic dielectric materials such as polyimides, polyamides, parylenes, polyacrylates, benzocyclobutene, fluoropolymers (e.g., amorphous fluoropolymers such as those sold under the brand name "Cytop" by Asahi Glass), polyvinyl alcohol and other polymers. A layer of such dielectric material is formed on top of gates 412, 416 and 418 and flexible substrate 400 using any deposition or film-forming method known in the art to provide gate insulator 410. Typically, gate insulator 410 is from about 100 to about 1000 nm thick.

Source electrodes 422, 434, and 440 and drain electrodes 426, 436, and 442 are positioned on top of gate insulator 410 and may be comprised of any suitable conductive metal, metal alloy, metal oxide or metal oxide alloy that contains at least one conductive metal (preferably, a highly conductive metal) or metal oxide. The source and drain electrodes could also be comprised of a conductive polymer such as poly(3,4-ethylenedioxythiophene):polystyrene sulfonate (PEDOT: PSS), especially biocompatible conductive polymers. Other conductive materials such as carbon nanotubes could also be utilized. The materials used in the individual source and drain electrodes may be the same or different materials may be employed in different source and drain electrodes. Conductive metals are well known in the art and include, without limitation, platinum (Pt), palladium (Pd), aluminum (Al), gold (Au), tungsten (W), chromium (Cr), silver (Ag), copper (Cu), calcium (Ca) or titanium (Ti). The source and drain electrodes may be single layered, but alternatively the electrodes may comprise a stack of two or more metal layers, e.g., a metal stack of Cr and Au, with Au on top, or Ti and Pt, with Pt on top. The electrodes (unpatterned) can be formed on gate insulator 410 using conventional deposition processes such as evaporation, chemical vapor deposition, plasma-assisted chemical vapor deposition and sputtering, and patterned electrodes provided by conventional lithography and etching. Alternatively, a shadow mask may be used in directly forming the patterned electrodes on gate insulator 410. The patterned electrodes could also be directly written on gate insulator 410 by means of ink-jet, transfer, screen, offset, micro-contact, pad, flexographic or gravure printing using a metal-, metal precursor- or conductive polymer-containing ink or paste. Once the ink or paste is applied in the desired locations and pattern, further treatment of the printed gate insulator may be carried out to form the desired electrodes. For example, the metal precursor in the ink or paste may be converted to metal or any solvent or volatile carrier present in the ink or paste may be removed by heating or other drying procedure. Electroplating or electroless plating techniques may also be employed to form the patterned electrodes. Typically, the source and drain electrodes may be from about 20 to about 700 nm thick. Preferably, the source and drain electrodes are covered with a biocompatible, non-toxic material so that the system may be safely implanted into a living organism. However, this encapsulating material should preferably also be capable of having contact openings etched into it so that the source and drain electrodes may be connected to another conductive layer or other conductive elements on the surface.

Organic semiconductor layer 430 is formed over source electrode 422 and drain electrode 426 such that the organic semiconductor layer is in contact with both electrodes. Likewise, organic semiconductor layer 432 is formed over and is in contact with source electrode 434 and drain electrode 436 such that organic semiconductor layer is in contact with both electrodes and organic semiconductor layer 438 is formed over and is in contact with source electrode 440 and drain electrode 442 such that organic semiconductor layer 438 is in contact with both electrodes. Masking, selective deposition, etching or other known techniques may be utilized to control placement of the organic semiconductor layers.

Organic semiconductor layers 430, 432, and 438 are comprised of any of the known organic semiconductor materials. An organic semiconductor is any organic material that has semiconductor properties. A semiconductor is any compound whose electrical conductivity is between that of typical metals and that of insulating compounds. Single molecules, short chain (oligomeric) and long chain (polymeric) organic semiconductors are known. Examples of semiconducting small molecules (aromatic hydrocarbons, especially polycyclic aromatic hydrocarbons) are: pentacene and its derivatives, tetracene, anthracene, arylene diimides, oligothiophenes, phthalocyanines and rubrene. Examples of polymers are: polythiophene and its derivatives such as poly(3-hexylthiophene) and its derivatives, poly(p-phenylene vinylene) and its derivatives, F8BT, as well as polyacetylene and its derivatives.

There are two major classes of organic semiconductors, which overlap significantly: organic charge-transfer complexes, and various "linear backbone" polymers derived from polyacetylene, such as polyacetylene itself, polypyrrole, and polyaniline. Like inorganic semiconductors, organic semiconductors can be doped. Highly doped organic semiconductors, for example polyaniline (Ormecon) and PEDOT:PSS, are also known as organic metals.

Suitable semiconductor materials include, but are not limited to: pentacene, tetracene, hexathiopene, polythiopene, phthalocyanine, perylene diimide, naphthalene diimide and other like organic materials. Of these materials, pentacene is preferred in the present invention. Each organic semiconducting layer preferably is a thin film material having a thickness of about 5 microns or less. More preferably, each organic semiconductor layer has a thickness of from about 100 to about 1000 A. The organic semiconductor layers may be formed using any of conventional deposition processes that are well known in the art. For example, each organic semiconductor layer may be formed by molecular beam deposition, vacuum evaporation, sublimation, spin-on coating, dip coating, ink-jet or gravure printing, and other like deposition processes.

In one especially preferred embodiment of the invention, the organic semiconductor layers are formed using a solution-processable precursor, thereby avoiding costly vacuum deposition techniques. In particular, a Diels-Alder adduct of a reactant containing a functional group R and pentacene is employed to form a precursor, wherein functional group R is varied to provide solubility in different solvents which also allow compatibility with the printing of circuits (i.e. when ink-jet or gravure printing are used). A solution of the precursor is applied to the surface of the assembly where it is desired to form an organic semiconductor layer (by spin-coating, for example) and then heated (preferably in a nitrogen atmosphere) so as to dry the solvent and retro-convert the precursor to pentacene. For example, any of the compounds and methods described in U.S. Pat. No. 6,963,080 and U.S. Pat. No. 7,125,989, each of which is incorporated herein by reference in its entirety, can be adapted for use in the present invention.

If so desired, the various materials used to fabricate the flexible transistors to be part of an electrical sensor-effector circuit in accordance with the present invention may be selected or modified so as to provide a chemical sensor, i.e., a chemically sensitive field-effect device capable of sensing the presence of, and/or measuring the level or concentration of, different species such as ions, gases, hormones, immuno-compounds, cholesterol, glucose and other substances that may be present within a living organism (e.g., as constituents of blood and other bodily fluids, tissues or organs). Examples of some substances that may be of particular utility to sense in the brain include: neurotransmitters such as GABA, glutamate, and excitatory amino acids. The sensing mechanism may be based on the change in conductivity in an organic semiconductor induced by direct interaction with certain molecules. Alternatively, the detection of chemical species may happen indirectly, via the field effect, in response to exposure to a particular analyte species.

For example, the material utilized as the organic semiconductor may be modified to fine-tune its chemical and physical properties, wherein the molecular structure and/or morphology of the organic semiconductor may be adjusted to enhance selectivity and sensitivity (for instance, by introducing different substituents or functional groups on the polymer used as the organic semiconductor). It is possible to covalently integrate recognition elements directly with the organic semiconductor to provide highly specific interactions with analytes of interest. As an illustrative example of the foregoing concepts, alkyl or alkoxy side chains placed on a polythiophene backbone may alter the response of that polymer towards particular species. Different organic semiconductors may be employed in individual flexible transistors within the array, such that the array is rendered capable of selectively sensing multiple species or analytes.

In one particularly preferred embodiment of the invention, a self-assembled monolayer (not shown in FIG. 4A) is formed on the surfaces of the source and drain electrodes prior to deposition of the organic semiconductor material. The performance of the thin film transistor may be enhanced by the presence of such a self-assembled monolayer at the interface between the electrodes and the organic semiconductor layers. The self-assembled monolayer of the present invention preferably comprises a thiol compound, such as an alkyl thiol, aromatic thiol or carbodithiolate, although other suitable substances such as charge transfer complexes (e.g., TCNQ) may also be employed for purposes of modifying the electrode/organic semiconductor interface.

Modifying the metallic surfaces of the source and/or drain electrodes with self-assembling organic compounds such as aliphatic and/or aromatic thiols permits the production of OTFT devices exhibiting 1) both hole transport and electron transport (p and n type), i.e., ambipolar transport; 2) improved transport for both n- and p-type transport (as compared to analogous devices with non-modified electrodes); and 3) the potential to tailor the transport based on the type of compound used to modify the electrodes. Application of a monolayer of various organic compounds such as thiols, especially aliphatic or aromatic thiols, is used to achieve surface modification of the electrodes. Suitable thiols include, but are not limited to, ethanethiol, butanethiol, hexanethiol, perfluorobenzenethiol, 4-nitrobenzenethiol, thiophenol, 4-amino thiophenol, 2-napthalene thiol, 4-mercaptophenol, and 4-mercaptopyridine. Other suitable organic compounds include, but are not limited to, other heteroatom-containing compounds such as selenols, carbenes, amines and isocyanides (also known as isonitriles or carbylamines) as well as other sulfur- and nitrogen-containing compounds such as dithiolates and dithiocarbamates. The degree of improvement of n-type transport, in particular, varies with the type of organic compound monolayer used.

The self-assembled monolayer preferably is formed on the electrodes prior to deposition of the thin film of organic semiconductor material by subjecting the electrodes to a treatment process that is effective in forming a monolayer of the selected compound on the surface of the electrodes. Specifically, the monolayer is formed by immersing the structure in a solution containing the selected compound or mixture of compounds. The treatment process may be carried out at room temperature for a time period of from about 0.5 to about 24 hours. Elevated temperatures can also be used as long as the elevated temperature does not adversely affect the various layers of the structure. The self-assembling monolayer-containing solution may be a concentrated solution or, more preferably, it is a dilute solution in which the self-assembling monolayer compound is dissolved in a solvent such as ethanol, toluene, chloroform or tetrahydrofuran. In one embodiment of the present invention, a dilute solution containing from about 0.001 to about 0.01% of the selected compound is employed in forming the self-assembled monolayer. After treatment with the self-assembling monolayer compound, the structure is removed from the solution, rinsed in fresh solvent, dried and then the organic semiconductor layer is formed thereon. The drying step is typically conducted at a temperature of from about 25 to about 30 degrees C. for a time period of from about 1 to about 5 minutes. Other temperatures and times are also contemplated herein.

Electrode insulator 420 is a layer of dielectric material that is formed over the semiconductor layers 430, 432, and 438 and gate insulator 410 using any suitable deposition or film-forming method. Any of the conventional dielectric materials known in the art may be utilized, although preferably such material is flexible and thus is advantageously selected from organic dielectric materials such as polyimides, polyamides, parylenes, polyacrylates, fluoropolymers and other polymers. The dielectric material could also be a spin-on glass (SOG), such as an inorganic type of silicate-based SOG or an organic (resin) type of siloxane- or polysilazane-based SOG, which can be applied so as to provide a planarized surface with a controlled thickness.

Electrode 444 is formed on top of electrode insulator 420. This electrode 444 may be comprised of any suitable conductive material such as a conductive metal, metal alloy, metal oxide or metal oxide alloy that contains at least one conductive metal (preferably, a highly conductive metal), conductive carbon (carbon nanotubes) or a conductive polymer. Conductive metals are well known in the art and include, without limitation, platinum (Pt), palladium (Pd), aluminum (Al), gold (Au), tungsten (W), chromium (Cr), silver (Ag), calcium (Ca), copper (Cu) or titanium (Ti). Electrode 444 may be single layered, but alternatively the electrode may comprise a stack of two or more metal layers, e.g., a metal stack of Cr and Au, with Au on top, or Ti and Pt, with Pt on top. An unpatterned layer containing conductive metal can be formed on electrode insulator 420 using conventional deposition processes such as evaporation, chemical vapor deposition, plasma-assisted chemical vapor deposition or sputtering. Patterned electrode 444 is then created by conventional lithography and etching. Alternatively, a shadow mask may be used in directly forming the patterned electrode 444 on electrode insulator 420. Typically, electrode 444 may be from about 100 to about 700 nm thick.

Electrode 444 is connected to drain electrode 426, gate 416, and source electrode 440 by means of vias 428, 417, and 439, respectively. These vias may be formed by any suitable method known in the art. For example, a conductive via material may be deposited on each layer of the assembly as it is built up and then etched away except in the specific locations where the vias are desired, with masking being employed to control the etching process. Alternatively, the assembly or partial assembly is formed and an isotropic etch process used to selectively form holes where the vias are desired, the holes thus formed being filled with a conductive material such as a conductive ink.

Encapsulant layer 450 is formed over electrode 444 and electrode insulator 420. Any suitable dielectric material can be used for encapsulant layer 450, although it is generally preferred for such material to be flexible, biocompatible and biostable. Suitable materials for encapsulant layer 450 include, but are not limited to, polyimides, parylenes, polyamides, polyacrylates, fluoropolymers, the photoresist SU8 and other polymers. The dielectric material used for encapsulant layer 450 could also be a spin-on glass (SOG), such as an inorganic type of silicate-based SOG or an organic (resin) type of siloxane- or polysilazane-based SOG, which can be applied so as to provide a planarized surface with a controlled thickness.

Electrode 452 is formed on top of encapsulant layer 450. This electrode 452 may be comprised of any suitable conductive material such as a metal, metal alloy, metal oxide or metal oxide alloy that contains at least one conductive metal (preferably, a highly conductive metal). Organic conductors, such as conductive polymers (e.g., PEDOT:PSS), could also be utilized, as well as conductive carbon materials (e.g., carbon nanotubes). Preferably, the material or materials used to form electrode 452 are biocompatible and biostable. Conductive metals are well known in the art and include, without limitation, platinum (Pt), palladium (Pd), aluminum (Al), gold (Au), tungsten (W), chromium (Cr), silver (Ag), copper (Cu) or titanium (Ti). Electrode 452 may be single layered, but alternatively the electrode may comprise a stack of two or more metal layers, e.g., a metal stack of Cr and Au, with Au on top, or Ti and Pt, with Pt on top. An unpatterned layer containing conductive metal can be formed on encapsulant layer 450 using conventional deposition processes such as evaporation, chemical vapor deposition, plasma-assisted chemical vapor deposition or sputtering. Patterned electrode 452 is then created by conventional lithography and etching. Alternatively, a shadow mask may be used in directly forming the patterned electrode 452 on encapsulant 450. Less conventional methods for achieving deposition of the conductive metal or other conductive material on encapsulant layer 450 in the desired pattern may also be employed, such as ink-jet or gravure printing of metal-containing colloids or other materials capable of furnishing an electrically conductive electrode (optionally, a heating or drying or other processing step is carried out after such material is printed onto the encapsulant layer). Electroplating and electroless plating methods may also be utilized. In one embodiment, electrode 452 takes the form of a relatively thin layer. In another embodiment, however, at least a portion of electrode 452 projects out from the surface of the assembly so as to provide a post 454 that is capable of penetrating or extending into tissue or an organ. Electrode 452 is connected to drain electrode 442 by means of via 441, which can be formed by any of the methods described previously in connection with via holes 428, 417, and 439. Instead of using a post 454 to make contact within the tissue or organ, it is contemplated that the circuitry shown in FIG. 4A may be formed as a thin strand, having a thickness on the order of a few microns, and these strands may be pushed into the tissue or organ so that flat contacts such as contact 452 may make electrical contact directly with the internal tissue.

FIG. 4B is a cross-section diagram of an optical sensor corresponding to the sensor described above with reference to FIG. 3A. In addition to the materials described above, this circuit includes a photodiode formed from electrode layers 460 and 464 and organic semiconductor layer 462. The organic semiconductor layer 462 may include an electron transport layer, an emissive layer and a hole transport layer (not separately shown).

FIG. 4C is a cross-section diagram of an optical emitter corresponding to the sensor described above with reference to FIG. 3B. In addition to the materials described above, this circuit includes organic light-emitting diode (OLED) formed from electrode layers 470 and 474 and organic semiconductor layer 472. The organic semiconductor layer 472 may include an electron transport layer, an emissive layer and a hole transport layer (not separately shown).

The example embodiment includes arrays of high density electrodes, actively controlled through organic TFTs, along with analog conditioning circuits and a digital subsystem. The integration of the electrodes with the circuits allows the construction of a large array of electrodes while dramatically reducing the amount of wiring that is needed to access each electrode. This integration allows the fabrication of electrode arrays with densities and spatial coverage that were previously impossible using only passive techniques. Reducing the volume of intracranial wires and of the implantable electrode array system is also important in reducing the complications resulting from sensor implantation. Also, by careful circuit design one can reduce the power consumption and noise pick-up, which are essential requirements for in-vivo biomedical applications. In the example embodiment, the array may be configured to electrically couple multiple electrodes together to operate as a single unit. This allows portions of the array to operate at respectively different scales. It is contemplated that the array may be configured using the response engine 120, shown in FIG. 1, so that portions of the array may be automatically scaled in response to a recognized pattern or as a step in an algorithm to identify a pattern of activity.

Although the apparatus is described as being applied to brain tissue, it is contemplated that it may also be used with spinal cord, cranial and peripheral nerves, bladder and muscle tissue or around blood vessels, both for sensing (electrically, optically and chemically) for a variety of applications, including neural prostheses, brain and nerve-machine interfaces and functional electrical stimulation or control.

As described above, each input electrode or other sensor may be connected to its own amplifier. All outputs of these amplifiers in a given column are multiplexed together, and if needed, the outputs of all the columns can be multiplexed together as well. Rows of electrodes can be addressed using a simple shift register in which a token circulates around the register. By loading the register (from a PC) by a set of tokens, one can read out a specified region of interest. This can be dynamically changed as part of a real-time feedback system.

The above scheme is implemented with TFTs and electrodes on flexible, stretchable substrates. The TFTs and electrodes may be interconnected, for example, thru via holes across a biocompatible, parylene spacer layer that also encapsulates the TFT active layer.

Current organic TFTs show large contact resistances and variability. The present invention uses molecular assembly and doping of the organic semiconductor-electrode interface to lower the contact resistance and fabricate high performance organic TFTs. The device interfaces are engineered through chemical modification, materials selection, and process design to reduce device hysteresis and variability. Top contact as well as bottom contact devices may be utilized. For example, the TFTs used in the present invention may be bottom contact, bottom gate (BC-BG) devices, bottom contact, top gate (BC-TG) devices and/or top contact, bottom gate (TC-BG) devices. The circuit designs are implemented to be tolerant to device variability and/or use calibration methods to correct for TFT variation, a technique widely used in nanoscale analog circuits. Ambipolar TFTs may be formed using molecular assemblies to engineer device interfaces. This technique may be used to form functional CMOS organic circuits. The availability of a TFT that can function as both pmos and nmos is a key milestone that allows the construction of CMOS organic circuits whose performance, in terms of amplification, noise margins and power dissipation, are superior to PMOS circuits.

Figure 4D:
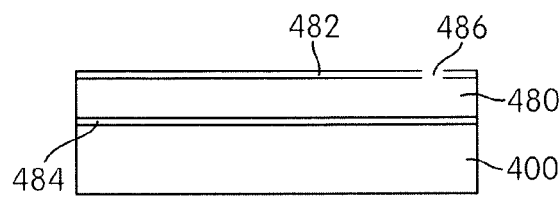

An example chemical effector is shown in FIG. 4D. The example effector includes a reservoir 480 formed as a space on top of the substrate 400. A first electrode 484 is formed on top of the substrate, at the bottom of the reservoir and a second electrode 482 is formed on top of the reservoir. During manufacture, the reservoir 480 is filled with a liquid chemical compound or solution which may be released by the sensor-effector array 110. When it is determined that the chemical compound is to be released, opposite electrical charges are placed on the two electrodes 482 and 484, causing pressure on the liquid in the reservoir. The chemical compound is then expressed through the opening 486 in the top of the reservoir.

Test Systems: Animal Experiments

Pilocarpine Induced Epilepsy in Rats: Using a model of epileptogenesis and chronic epilepsy that is well established in the Contreras laboratory, the model consists in the induction of a 1-3 hours status epilepticus (SE) in adult male Sprague Dawley rats (180-200 g) by systemic injection of the cholinergic agonist pilocarpine (400 mg/kg, s.c.). The status is terminated by an injection of diazepam (7.5 mg/kg, s.c.). Rats are monitored with continuous video and intracranial EEG beginning before induction of SE, through the epileptogenic process (lasting weeks) and for several weeks after they develop spontaneous seizures during daily life. Multiscale, high resolution recordings are obtained throughout this process using the example sensor-effector array, first to understand the signatures of epileptogenesis, and then employed with self-organizing recording and stimulation strategies in order to suppress abnormal discharges and lead the system into a more ordered, non-epileptogenic state. In a second portion of these experiments automated algorithms extract quantitative features from rats selected to have mild and stable epilepsy, (i.e., up to 1-2 seizures per day by 2-4 weeks after SE) in order to track and suppress the generation of individual seizures. The machine learning algorithms, described above, track the evolution of network activity towards seizures and consequently develop closed-loop, continuous control algorithms using microstimulation strategies to arrest the process and drive the system back into a normal baseline state.

Ketamine-Induced Schizophrenia-like state in mice and genetically modified mice: A recent key finding in the pathophysiology of schizophrenia is glutamatergic hypofunction, in particular of NMDA type transmission. Consequently, we have being studying two models that mimic aspects of the schizophrenic phenotype. They are (i) normal mice after the injection of the NMDA blocker ketamine and (ii) mice lacking the gene for Neuregulin-1. This protein is associated with NMDA type glutamatergic transmission and has been shown to be altered in post-mortem genetic analysis of brains from patients with schizophrenia. These models and their normal controls are used to characterize the spatiotemporal distribution of gamma oscillations in response to visual stimulation with drifting gratings of varying orientation and grating spatial frequency while recording from the primary visual cortex. The visual stimulation paradigm has been developed for acute anesthetized mice and may be used to test example sensor-effector arrays. A key component of this set of experiments is the characterization of normal patterns of activity that vary between animals, and the response to stimulation protocols coupled to machine learning algorithms designed to drive quantitative parameters extracted from cellular activity back toward the normal, control state. Such large scale characterization and stimulation experiments have never been done due to the lack of suitable high density and flexible recording devices such as those provided by the example embodiment.

The example embodiments described above are a new class of flexible implantable electronic devices capable of sensing and effecting electrical and chemical signals in the body that will open unprecedented access to probe brain function, organization at the system level, and to diagnose and treat brain network disorders.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A flexible sensor-effector circuit comprising:
  a first flexible transistor having source and drain electrodes defining a first conductive path and a first gate electrode configured to control the conductivity of the first conductive path;
  a second flexible transistor having source and drain electrodes defining a second conductive path and a second gate electrode configured to control the conductivity of the second conductive path; and
  a transducer coupled to the drain electrode of the first transistor and to the gate electrode of the second transistor, wherein the first transistor is coupled to an effector circuit and the second transistor is coupled to a sensor circuit.

2. The flexible sensor-effector circuit according to claim 1, wherein the first and second transistors are organic field effect transistors.

3. The flexible sensor-effector circuit according to claim 1, wherein the transducer includes a chemical sensor.

4. The flexible sensor-effector circuit according to claim 1, wherein an organic semiconductor is formed over said source and drain electrodes and said source and drain electrodes have a self-assembled monolayer formed thereon.

5. The flexible sensor-effector circuit according to claim 1, wherein said first flexible transistor and said second flexible transistor are ambipolar.

6. The flexible sensor-effector circuit according to claim 1, wherein said source and drain electrodes are formed on a surface of a dielectric substrate.

7. The flexible sensor-effector circuit according to claim 1, wherein said first flexible transistor and said second flexible transistor are encapsulated.

8. An array of sensor-effector transducers, comprising:
a flexible substrate;
a plurality of flexible electrical sensor-effector circuits, each comprising:
    a first flexible transistor formed on the substrate having source and drain electrodes defining a first conductive path and a first gate electrode configured to control the conductivity of the first conductive path;
    a second flexible transistor formed on the substrate having source and drain electrodes defining a second conductive path and a second gate electrode configured to control the conductivity of the second conductive path;
    a sensor-effector transducer coupled to the drain electrode of the first transistor and to the gate electrode of the second transistor, wherein the first transistor is coupled to an effector circuit and the second transistor is coupled to a sensor circuit;
    a flexible select transistor having a conductive path defined by a source electrode and a drain electrode and a select gate electrode configured to control the conductive path of the select transistor, wherein the source electrode of the select transistor is coupled to the sensor-effector transducer and the drain electrode of the select transistor is coupled to the drain electrode of the first transistor and to the gate electrode of the second transistor and wherein the gate electrode is coupled to a select signal and configured to control the conductive path of the select transistor in response to the select signal.

9. The array of sensor-effector transducers according to claim 8, further including a plurality of optical sensor circuits, each optical sensor circuit comprising:
a photosensor formed on the substrate;
a photo select transistor having a conductive path defined by a source electrode and a drain electrode and a gate electrode configured to control the conductive path of the photo select transistor in response to a control signal wherein the source electrode of the photo select transistor is coupled to the sensor-effector transducer and the drain electrode of the select transistor is coupled to the drain electrode of the first transistor and to the gate electrode of the second transistor and the gate electrode of the select transistor is coupled to a select signal; and
an amplifier coupled to the photosensor to provide an electrical signal corresponding to an amount of light received by the photosensor at an output terminal.

10. The array of sensor-effector transducers according to claim 9, further including a plurality of organic light-emitting diodes (OLEDs).

11. The array of sensor-effector transducers according to claim 10, wherein the plurality of OLED's are configured on the array such that each OLED is adjacent a respective one of the optical sensor circuits.

12. A sensor-effector system comprising:
an array of sensor-effector transducers for providing a plurality of sensed signals and for applying a plurality of effector signals;
input signal conditioning circuitry, coupled to the array of sensor-effector transducers for digitizing the plurality of sensed signals;
a processor coupled to the array of sensor-effector transducers for receiving the digitized signals, the processor including computer program instructions which cause the processor:
    to process the plurality of signals to transform the plurality of digitized signals into multiple feature vectors;
    to analyze the multiple feature vectors to identify patterns in the multiple feature vectors and to classify the identified patterns; and
    to generate at least one response vector resulting from the recognized pattern; and
output signal conditioning circuitry, coupled to the processor to convert the response vector to at least one analog signal and to apply the at least analog signals as at least one of the plurality of effector signals applied to the array of sensor-effector transducers.

13. The sensor-effector system according to claim 12, wherein the array of sensor-effector transducers includes a plurality of sensor-effector electrodes configured to sense and apply electrical signals as the sensed signals and effector signals, respectively.

14. The sensor-effector system according to claim 13, wherein the array of sensor-effector transducers further includes a plurality of optical emitters configured to emit respective optical signals as the effector signals in response to respective electrical stimuli.

15. The sensor-effector system according to claim 14, wherein the optical emitters are organic light-emitting diodes (OLEDs).

16. The sensor-effector system according to claim 14, wherein the array of sensor-effector transducers further includes a plurality of optical sensors configured to sense optical signals and convert the optical signals into respective electrical signals and to provide the respective electrical signals as ones of the plurality of sensed signals.

17. The sensor-effector system according to claim 12, wherein the input signal conditioning circuitry includes transform circuitry to transform the digitized signals from time-domain signals to frequency-domain signals.

18. The sensor-effector system according to claim 17, wherein the transform circuitry includes one of fast-Fourier transform circuitry or wavelet transform circuitry.

19. The sensor-effector system according to claim 12, wherein the computer program instructions that cause the processor to analyze the multiple feature vectors to identify patterns in the multiple feature vectors and classify the identified patterns include at least one of:
computer program instructions that implement a hidden-Markov model classifier;

computer program instructions that implement a support vector machine classifier; or computer program instructions that implement a frequent itemset mining classifier.

20. The sensor-effector system according to claim 12, wherein:

the plurality of sensed signals include time-varying electrical signals; and the plurality of effector signals include time-varying electrical signals synchronized to the respective plurality of sensed signals, wherein the plurality of effector signals are approximately opposite in phase to the respective plurality of sensed signals and approximately equal in amplitude to the respective plurality of sensed signals.

* * * * *